United States Patent [19]  [11] 3,983,344
Straihammer  [45] Sept. 28, 1976

[54] OPERATED SWITCH CONTROLLER FOR DENTAL ENGINE AND ASSOCIATED APPARATUS

[75] Inventor: Reinhard Straihammer, Kirschhausen, Germany

[73] Assignee: Siemens Aktiengesellschaft, Erlangen, Germany

[22] Filed: June 19, 1973

[21] Appl. No.: 371,544

[30] Foreign Application Priority Data
June 26, 1972 Germany............................ 2231234

[52] U.S. Cl.................................. 200/86.5; 32/23; 74/478; 200/153 C
[51] Int. Cl.²...................... H01H 3/14; A61C 1/00; G05G 9/00
[58] Field of Search............ 32/22, 23, 28; 192/129; 74/478, 478.5, 512; 338/47, 78, 108, 153, 215; 200/61.89, 86.5, 153 C; 318/446, 551; 312/209

[56] References Cited
UNITED STATES PATENTS

| 543,855 | 8/1895 | Denison | 318/551 X |
|---|---|---|---|
| 804,595 | 11/1905 | Garhart | 318/551 X |
| 2,651,351 | 9/1953 | Lauterbach | 200/86.5 X |
| 2,671,268 | 3/1954 | Crawford | 32/23 |
| 2,857,493 | 10/1958 | Tascher | 200/86.5 |
| 3,296,698 | 1/1967 | Staunt | 32/28 |
| 3,471,928 | 10/1969 | Billin | 200/86.5 X |
| 3,502,833 | 3/1970 | Rossini et al. | 200/86.5 |
| 3,598,947 | 8/1971 | Osborn | 200/86.5 |
| 3,742,167 | 6/1973 | Muther | 200/86.5 |
| 3,833,782 | 9/1974 | Bartel | 338/153 X |

Primary Examiner—James R. Scott
Attorney, Agent, or Firm—Haseltine, Lake & Waters

[57] ABSTRACT

A foot control installation, which is particularly adapted for use in a dental apparatus, in which an actuating member, operatively connected to a control and/or switching element, is supported in a housing of the dental apparatus, and is adapted to have movement imparted thereto, with one end of the actuating element projecting from the housing and having a foot contact. The foot control installation includes a foot-actuated pressure plate and downwardly depressable foot contact for actuating switches whereby, in addition to the control of the speed, other switching sequences are concurrently provided, for example, the predetermination of the rotational direction of the motor, the in-and-out switching of the motor, as well as the switching of a valve used for the supply of pressurized air or water to the handpiece of the drilling apparatus.

15 Claims, 9 Drawing Figures

OPERATED SWITCH CONTROLLER FOR DENTAL ENGINE AND ASSOCIATED APPARATUS

FIELD OF THE INVENTION

The present invention relates to a foot control installation, and which is particularly adapted for use in a dental apparatus, in which an actuating member, operatively connected to a control and/or switching element, is supported in a housing of the dental apparatus, and is adapted to have movement imparted thereto, with one end of the actuating element projecting from the housing and having a foot contact.

Foot control installations of this type are generally utilized in the dental technology for controlling the rotational speed of drill drives or motors. As a rule, in addition to the control of the speed, other switching sequences are concurrently provided, for example, the predetermination of the rotational direction of the motor, the in-and-out switching of the motor, as well as the switching of a valve used for the supply of pressurized air or water to the hand-piece of the drilling apparatus.

DISCUSSION OF THE PRIOR ART

Due to the multiplicity of actuating elements required for that type of foot control installation, it is frequently quite difficult for a dentist to, as needed, accurately locate and rapidly actuate the correct desired actuating elements. Frequently, the actuating elements of the frequently manipulated switches are also quite similarly shaped, and located on the upper surface of a housing so as to be able to be reached and actuated only by means of extensive foot manipulations. However, a shifting of the foot position is concurrently combined with relative shifting of the body weight from one foot to the other. The frequent change in the foot positions becomes, however, over extensive periods of time rather tiresome for the doctor or dentist and may easily lead to erroneous switching and control sequences being effected during control operation.

Inasmuch as the foot control installations are generally located positioned externally of the field of vision of the operator during operation, and since switching and control sequences must be effected frequently during delicate operations, in view of which the operator's vision cannot be directed toward the foot control installation, the installation must provide that the actuating elements for at least the most frequently utilized switches must be easily reachable and adapted to be accurately actuated.

SUMMARY OF THE INVENTION

Accordingly, it is an object of the present invention to provide for a foot control installation of the above-described type, affording a simplified actuation of the switching and control elements to the operator. In particular, the present invention facilitates that the actuating elements of the most frequently utilized switches are adapted to be manipulated without requiring extensive motion of the operator's foot. Furthermore, the foot control installation may be constructed so that these switches may be actuated in a practically "blind" operative sequence.

According to the present invention, the foregoing is attained in that on the upper surface of the housing and proximate to the path of movement of the foot contact there is located an actuating element adapted to actuate a switching element in response to downward displacement thereof. The actuating member may be located above the full path of movement of the foot contact defined by the displacement of the actuating member from an initial into an operative end position. It is advantageous that the actuating element be constructed in the shape of a large-surfaced foot pressure or step plate. The step plate may be supported so as to be tiltable about an axis extending in substantially parallel relationship with respect to the linear path of movement of the actuating element. The foregoing provides not only for an aesthetically attractive but also practical actuatable installation when, it is proposed, in a further embodiment of the invention, that the step plate be made desk-shaped or formed in a sloped position in which the slope extends toward the foot contact. A particularly advantageous correlation between the control installation and the shape of the actuating foot is provided when the plate slope extends at an angle of $\alpha = 3$ to $10°$, and preferably $5°$, with respect to the support surface of the housing, which generally coincides with the lower surface of the base plate of the housing. By locating the actuating elements along the upper surface of the housing, the advantage is obtained that in a control installation having an actuating element projecting outwardly of the housing, the foot contact may be connected with a further actuating member which is responsive to downward foot pressure being applied thereto, and which is operatively connected to another switching element. The foregoing becomes difficult or impossible when a pressure plate is positioned below the actuating element, since upon downward pressure being exerted upon the actuating element which is connected to the foot contact, the step plate is liable to be actuated so as to effect an undesirable switching sequence. The advantage of the invention accordingly lies in that the actuating element and particularly the foot contact, in addition to the horizontal displacement effecting the actuation of the control elements, further provides for the actuation of another switching element by by depression of the foot contact. Finally, the actuating member may also be associated with a preferably detachable locking arrangement which is effective in the operative end position thereof. Furthermore, a selector switch may be operatively connected with the locking arrangement, which provides for selective operation of the switching element operating in conjunction with the actuating member, or with the further switching element utilized for the in-and-out switching of the motor drive operating in connection with the actuating member during displacement of the latter from its initial position. By means of the foregoing, the foot control installation is universally operable. The installation may be utilized either for the black-white switching for maximum rotational requirement (variation of the rotational speed is obtained if desired by means of an external control element relative to the foot control installation, for example, a hand-actuated element manipulated by the operator, or the in-and-out switching and control of the rotational speed by means of the actuating member. The distance between the sloped step plate proximate to the foot contact and the tilting axis is relatively large, so as to provide a sufficient switching path even at relatively small plate tilting angles.

BRIEF DESCRIPTION OF THE DRAWINGS

Further advantages may be ascertained as follows in the detailed description of exemplary embodiments of the invention, taken in conjunction with the accompanying drawings, in which.

DETAILED DESCRIPTION

Figure 1:
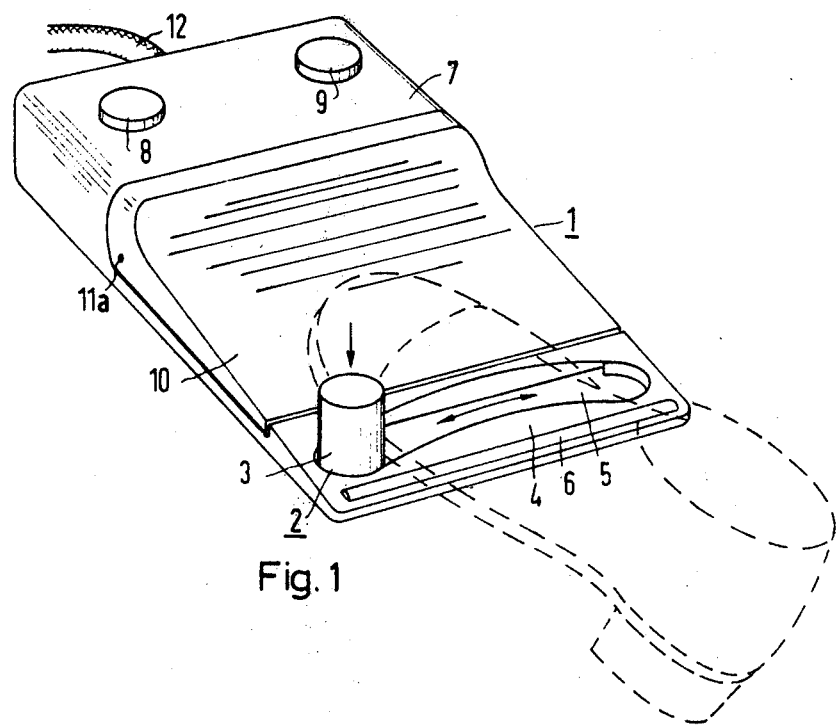
FIG. 1 illustrates in a perspective view a foot control installation according to the present invention.

Referring now in detail to FIG. 1 of the drawings, there is illustrated in a perspective view a foot control installation, as utilized for dental apparatus, for example, dental drill drives or motors. The foot control installation includes, in plan view, a rectangular housing 1 having an actuating member 2 projecting therefrom, which is adapted to be displaced or actuated by the foot of an operator. The actuating member 2 is provided with a foot contact 3, and may be moved in the directions of the illustrated arrow from an initial position into operative positions. In its initial position, the actuating member (arm 28 in FIG. 3) extends approximately parallel to the two lengthwise sides of the rectangular housing 1. The distance of the initial position with respect to an operative end position of the foot contact (in the Figure, one operative end position is illustrated) defines the path of movement of the actuating element, as well as that of the foot contact. The center or intermediate position of the actuating element between the two operative end positions forms its initial position. In the region of foot contact 3 there is provided a foot step saddle or frame 4 which includes an aperture 5 in the area of the path of movement of the foot contact. The step frame 5 assures that upon manipulation of the actuating element, the control installation does not slide relative to its supported position. The step frame has its lower surface located in the plane of the support surface of the housing 1 which, in this instance, coincides with the bottom surface of a base plate 13 supported on the floor. A plastic material strip or runner 6 having an upwardly curved upper surface is positioned in a recess formed in step frame 4 so as to afford the advantage that upon the operator stepping onto the step frame only a relatively small upper surface portion thereof is subject to a weight or load. Consequently, the foregoing assures that only relatively low frictional forces are produced between the sole of the foot and the plastic material runner 6, while nevertheless the entire weight load may be conducted to the support (floor). The operator can thereby easily manipulate the actuating member with his foot, without the housing being displaced relative to its position on the floor.

In the rear portion 7 of the housing 1 there are positioned, at its upper surface, two actuating elements 8 and 9 which are operatively connected to switching elements located interiorly of housing portion 7. The support for actuating member 2 is also located in housing portion 7. A foot step or pressure plate 10 extends between housing portion 7 and the forward portion of the foot control installation, and is supported so as to be tiltable about an axis 11 which extends in parallel to the linear path of movement of the actuating member. The step plate 10 is desk-shaped and is sloped upwardly at an angle of $\alpha = 3$ to $10°$ from the foot contact 3, curving in the final third of its slope upwardly toward an angle $\beta$ of approximately $140°$, and finally joining into the upper surface of housing portion 7. A common inlet conduit is designated by numeral 12, within which the individual electrical conduits leading to the switching and control elements are conveyed into housing 1.

Figure 2:
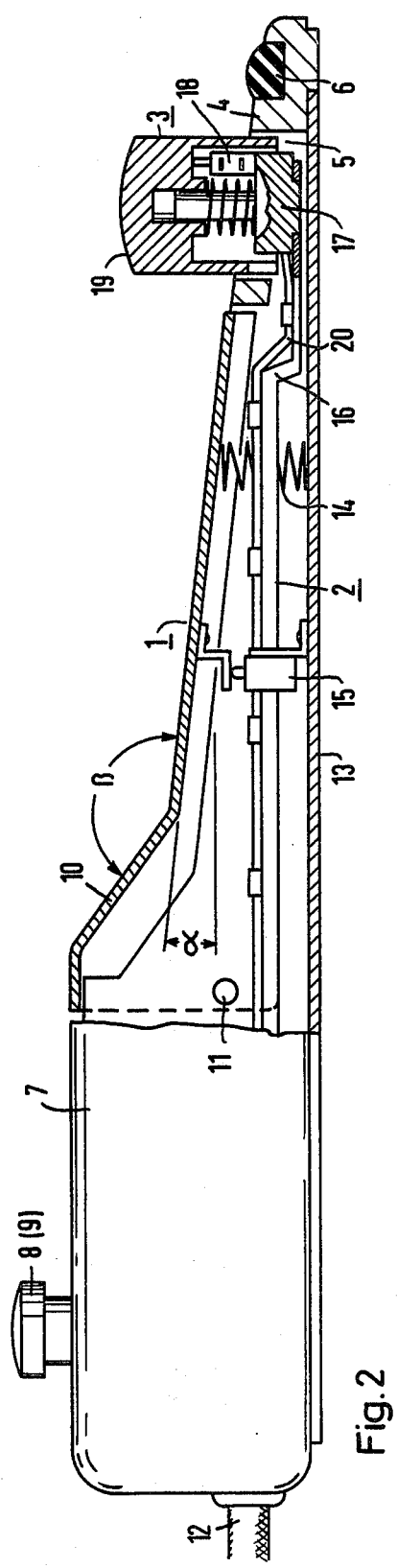
FIG. 2 shows the foot control installation of FIG. 1 in a side view, partly in section.

FIG. 2 illustrates the control installation in a side view, in which the forward portion thereof is shown in section. The angle $\alpha$ is designated with respect to the horizontal upper surface of the housing which normally corresponds with the bottom surface of the base plate 13, and the angle $\beta$ with reference to the upper surface of the sloped portion. Upon the operator stepping onto the step plate 10, the latter is tilted about axis 11 in opposition to the biasing force of a spring 14, so as to actuate a switch 15.

As may be ascertained from FIGS. 1 and 2, the step plate 10 extends across the full width of the foot control installation. This renders it possible to provide the desired switching sequence for each operative position of the actuating element 2 by means of a single switch without requiring any large degree of foot motion. The location of the step plate 10 above an arm 16 of the actuating member 2 allows for the connection of the foot contact 3 with a switching member which is actuated by stepping downwardly thereon. This would be rather difficult by positioning a switching bar or runner below arm 16, since this would create the danger that upon axial actuation of the foot contact, the switching runner is concurrently actuated therewith so as to thereby effect an undesired switching sequence. Consequently, the arm 16 of actuating member 2 is provided with an extension 17 which, together with a cap-shaped actuating element 19, forms a switch housing for a switching element 18. A switch supply conduit 20 for the switching element 18 is introduced into extension 17 through a suitable bore, and fastened along arm 16 by means of suitable collars or clamps. The function of both switching elements 15 and 18 is explained in the schematic circuit diagram of FIG. 9.

Figure 3:
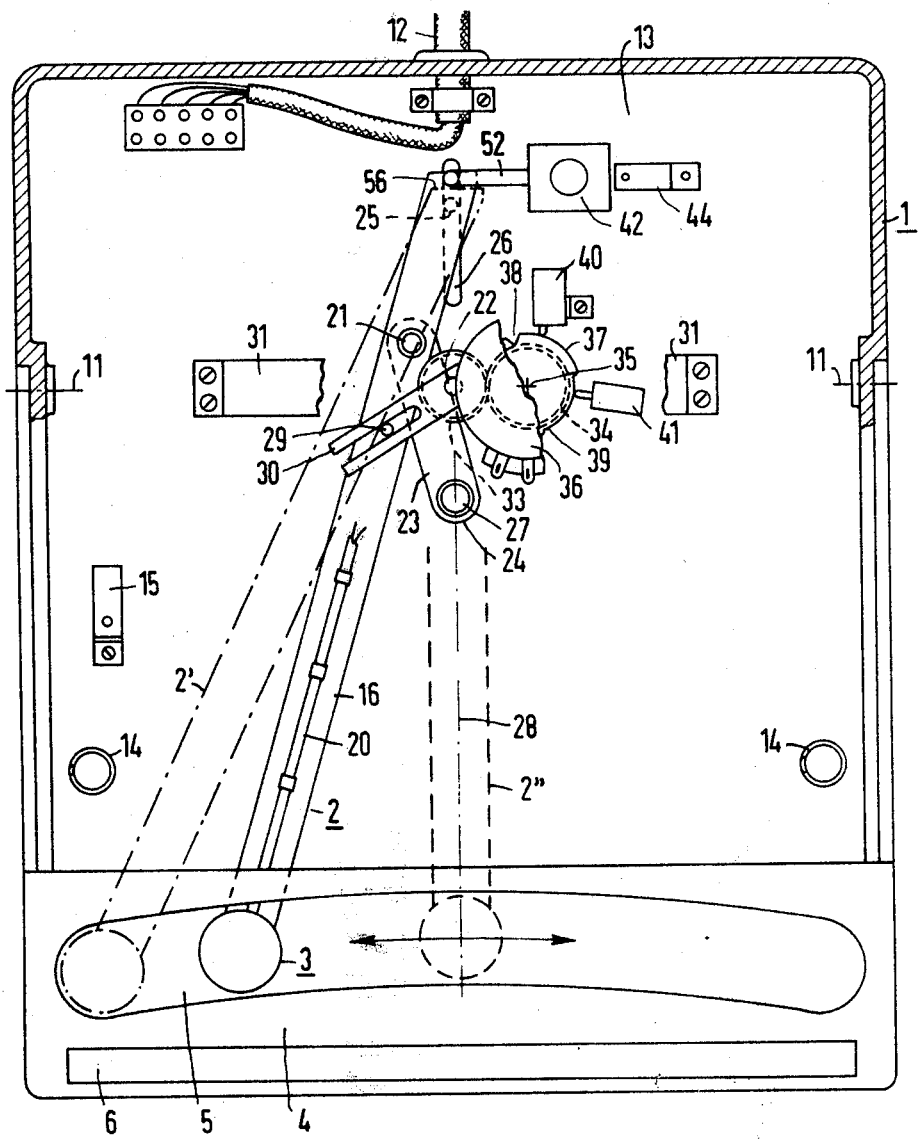
FIG. 3 shows the foot control installation of FIG. 1 in a top plan view without the foot step or pressure plate and housing.

In FIG. 3 there is illustrated, in plan view, a control installation with the housing 1 and step plate 10 not shown for purposes of clarity. The arm 16 of the actuating member 2 is supported at two locations on base plate 13. A first support 21 is located in proximity to foot contact 3, and a second support 25, 26 is located remote therefrom. The support 21 is a basically pivotal support and is constructed by the connection of the free end of a stationarily mounted single-arm pivot lever 23 to arm 16. The stationary support is designated by reference numeral 24. The support 25, 26 consists of a support projection 25 and a cooperative support which, in effect is a guide path 26 formed in the base plate 13. A support axis 27 for the support 24 coincides with the illustrated center line 28 of the actuating member 2 shown in its initial position. The support 21 is conveyed by means of pivot lever 23, as viewed from the foot contact, along a concavely curved path, while the support projection 25 of the second support, and which is mounted on the actuating member, is conveyed through the linear path of movement so that the support projection 25, upon displacement of the actuating member, is presently moved in the direction of the foot contact in the initial position of the actuating member.

A follower pin 29 which is fastened onto the arm 16 of the actuating member 2 extends into contact with the slot of a fork 30, the latter of which is rotatably journaled on a frame element 31 fastened in base plate 13. A ratchet or gear wheel 33 is mounted on the support axis 32 (FIG. 4) of the fork 30, and engages a gear 34 which in turn is fastened onto the axis 35 of a potentiometer 36. A plate cam 37 having cutout portions 38 and 39 is also supported on the axis 35 of the potentiometer 36. Through plate cam 37 there may be actuated two switching elements 40 and 41 which are adapted to provide a switching sequence described in greater detail in the circuit diagram of FIG. 9.

A locking arrangement 42 is associated with the actuating member 2, by means of which the latter may be arrested in both of its operative end positions to either the left or right of its initial position. In the Figure the left-hand operative end position of the actuating member 2 is illustrated in chain-dotted lines (designated by 2'). In this position the potentiometer 36 is fully effective, in essence, a rotary drive controlled by the potentiometer is operated at its maximum rotational speed. The intermediate or initial position of the actuating member is shown in chain-dot in FIG. 3 of the drawing (designated 2"). The function of the individual switching elements 40, 41 and 44, as well as that of the potentiometer 36, is detailed in connection with the description of the circuit diagram of FIG. 9.

The support of the actuating element 2 in the above illustrated and described manner has the advantage in that the foot contact 3 is conveyed, upon manipulation of the actuating member 2 from its initial position (illustrated by chain-dotted lines 2") in a substantially linear to concavely curved path, as viewed from the foot contact.

This affords the advantage that the foot contact 3, unlike prior art foot control installations, has no motion tending to move away from the foot tip of the operator, but in contrast the foot contact is moved toward the direction of the foot tip. Consequently, this largely eliminates the possibility of slippage occurring between the foot tip of the operator and the foot contact, even during relatively large displacement of the actuating member.

Figure 4:
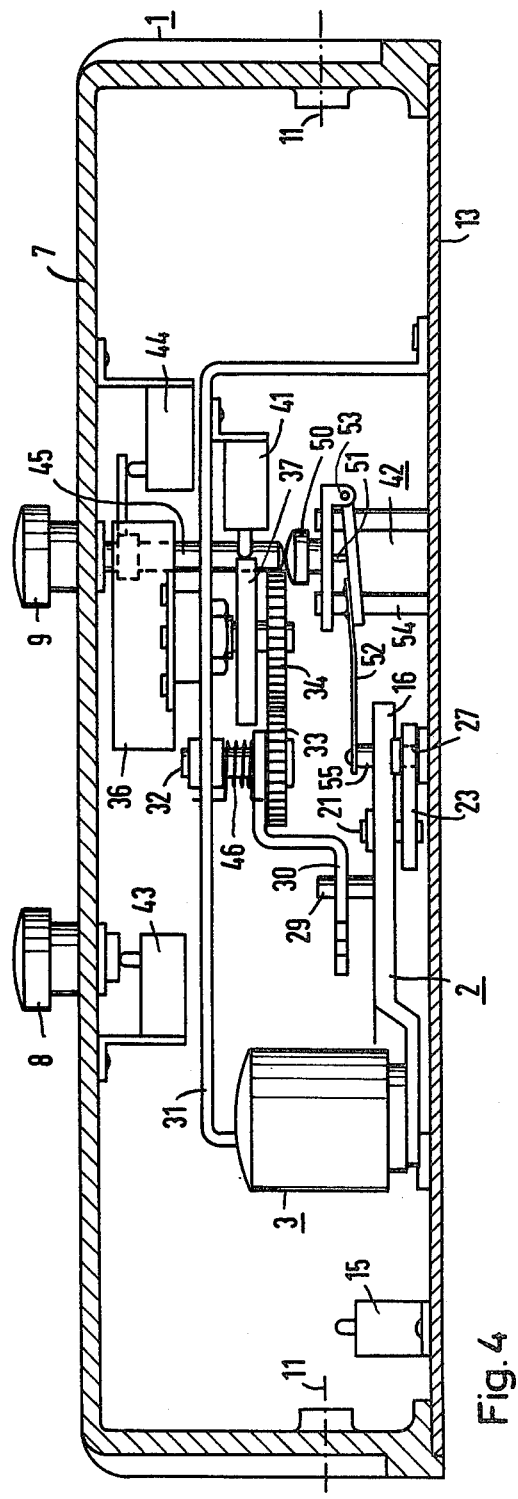
FIG. 4 shows a front elevational view of the foot control installation; with the housing illustrated in section.

The control installation is shown in front view in FIG. 4, in which for illustrative purposes the housing is represented sectioned in a transverse plane. The actuating element 8 is operatively connected with a switch element 42, and the control element 9 with a switch element 44. By means of the last mentioned element, the locking arrangement 42 in FIG. 3 is actuated by means of a contact projection 45 which is connected with actuating element 9. A return spring 46 is mounted on the axis 32 of fork 30, contacting at one end thereof fork 30 and at the other end element 31 whereby the actuating element 2 is always biased thereby from any operative position deviating from its initial position back into its initial position. The functions of switching elements 42 and 44 are explained in further detail in the schematic circuit diagram of FIG. 9.

Figures 5, 6:
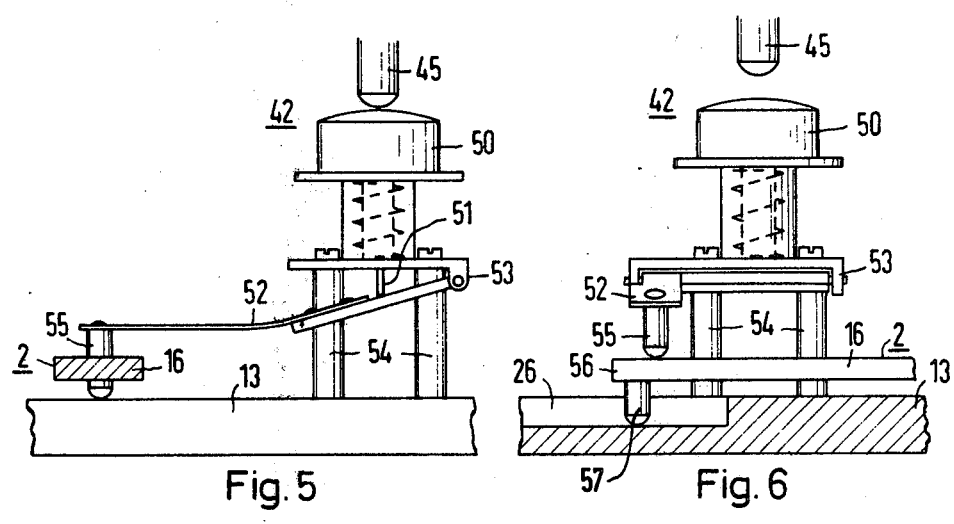
FIG. 5 shows a locking arrangement for the actuating element of the foot control installation in a front plan view.
FIG. 6 illustrates the locking arrangement of FIG. 5 in side elevational view, partly in section.

Details of the locking arrangement are illustrated in FIGS. 5 and 6 of the drawing. In FIG. 5, the locking arrangement is shown in a frontal view, comparably to that of FIG. 4; and in FIG. 6 is shown in a side elevational view. The locking arrangement 42 includes a spring-loaded pressure knob 50 which contains therein a locking mechanism of the type found in the actuating arrangement of a ball writer or pen. With the above mechanism, which is not further described, there is connected a pressure pin 51, which presses onto a leaf spring 52 which is mounted on a retainer 53. The retainer 53 is connected with the base plate 13 by means of support columns 54. The leaf spring 52 includes a pressure pin 55, which in its unlocked positions resiliently contacts the upper surface of arm 16 of the actuating member 2, and in its locked position (locking arrangement) extends behind of the rear edge 56 of arm 16 of the actuating member 2 so as to arrest the latter in that position. In FIG. 5 the locking installation is shown in its locked relationship (also illustrated in chain-dotted lines in FIG. 3), and in FIG. 6 in its unlocked position.

The advantage of the above described locking installations consists of in that the locking sequence may be effected in any desired predetermined position of the actuating member, when the actuating element 9 is downwardly depressed. By means of the mechanism located within the pressure knob 50, the pressure pin 51 is pressed against the leaf spring 52, and consequently the pressure pin 55 is spring-biased against the upper surface of arm 16. When the actuating member 2 reaches its operative end position (left or right) the pressure pin 51 snaps behind the rear edge 56 and thereby locks the actuating member 2 against any return movement into its initial position. Release or unlocking is effected upon pressure is again applied to the actuating element 9. This causes the release of knob 50, the pressure pin 51 springs upwardly and the leaf spring 52 is, in response to its spring effect, raised above the rear edge of the arm 16, so as to permit the actuating element 2 under the influence of return spring 46 to be returned to its initial position (FIG. 4).

Figure 7:
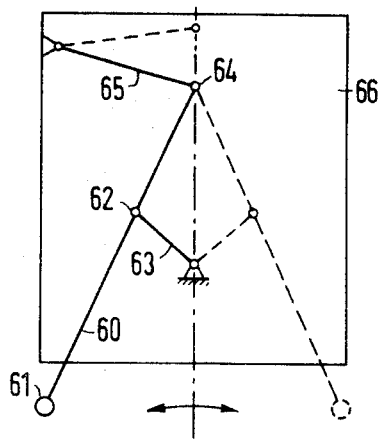
FIG. 7 illustrates schematically the support for the actuating element in a further embodiment thereof.
Figure 8:
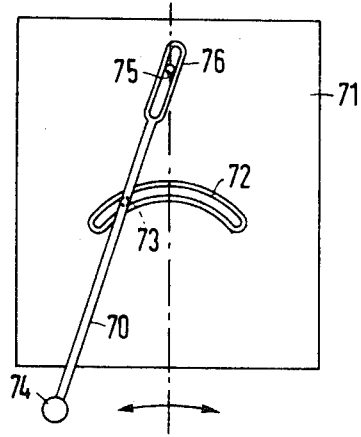
FIG. 8 illustrates schematically a further embodiment of a support for the actuating element.

FIGS. 7 and 8 of the drawing illustrate in a greatly simplified representation further embodiments of the construction and support of the actuating element 2. In the embodiment shown in FIG. 7 of the drawing, an actuating element 60 includes proximate to the foot contact 61 (similar to the embodiment of FIG. 3) a first support 62 which is formed by linkage connection of a rod 63, and a second support 64 which is formed by the connection of a pivot arm 65. The pivot point of the pivot arm 65 on the base plate is determined so that the pivot arm 65 in the initial position of the actuating element 60 (shown in chain-dotted lines) extends approximately at a right angle relative to a connecting line between the second support and the foot contact in the initial position of the actuating element. When the actuating element is symmetrically constructed, this connecting line corresponds to the symmetrical axis of the actuating element. In order to obtain a substantially linear movement for support 64, it is advantageous that the pivot arm 65 be formed as lengthy as possible, whereby the pivot support 64 describes an extremely shallow curved until approximately linear path of movement.

In the embodiment of FIG. 8 of the drawings, an actuating member 70 is guided in a concavely curved guide path 74 located in the base plate 71, as viewed from the foot contact 74. A support portion 73 located on the actuating member may be constituted of a slide bushing or roller. The support 75, 76, which is located remotely from the foot contact 74, is a linear guide. In this connection, the support portion 75 is located on the base plate 71, and the support portion 73 on the actuating member 70.

The advantage of all of the embodiments shown in the figures lies in that, in an extremely simple technological construction there is obtained, as viewed from the foot contact, a concavely curved toward almost a linear path of movement for the foot contact, so as to effectively prevent the actuating element moving away from the foot tip of the operator, when the actuating member is moved from its initial position.

Figure 9:
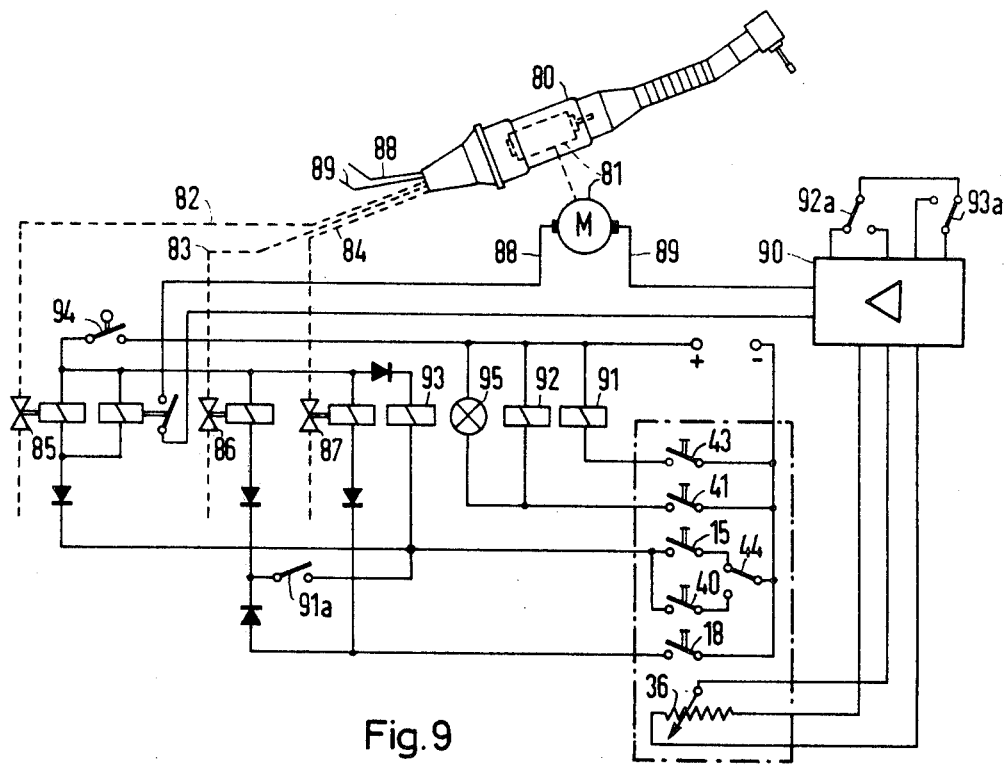
FIG. 9 shows a schematic circuit diagram for another embodiment of the control installation utilized with an electric motor-driven dental hand drill.

In FIG. 9 of the drawing there is illustrated the functional interconnection of the individual control and switching elements with regard to an exemplary embodiment.

Thus, a dental hand drill 80 is driven by an electric motor 81, and includes pressure conduits 82 through 84 for, respectively, the supply of cooling air, spray water and spray air. The control over the foregoing supply is obtained by means of magnetic valves 85, 86 and 87. The electrical inlet conduits for the motor 80 are designated by reference numerals 88 and 89. The conduit 89 extends from the motor into a suitable transformer switch 90 generally utilized for such had motors, which is adapted to ensure that the rotation of the motor corresponds with that of the variation sensed by potentiometer 36 in response to the displacement of the actuating element. The control installation may further be provided with a switch arrangement for maintaining constant the rotational speed of the motor during any load variations, as well as safety arrangement against overloading of the motor. This type of amplifying or transformer circuit may be constructed in various different manners. The construction thereof has no bearing with respect to the present invention, in view of which the disclosure does not detail any particulars with respect to such switching arrangements.

The switching and control elements contained in the foot control installation are encompassed in chain-dotted representation, and have the from upwardly to downwardly listed following functions. By means of switch 43 (actuated by actuating element 8 shown in FIG. 4) through its switch contact 91a and across relay 91 there is provided for the supply of spray water to the hand drill. The switch 41 (actuated by the plate cam 37 shown in FIG. 3) switches the relay 92 with its switch contacts 92a and reverses the direction of rotation of the motor, inasmuch as both contact poles of the motor are reversed within the amplifying switch 90. By means of switches 15 and 40 (switch 15 is actuated by pressure being imparted to step plate 10, and switch 40 is actuated through plate cam 37) the motor is actuated, in which voltage is conveyed to the motor through relay 93 and corresponding switch contact 93a. A prerequisite is that the switch 94, which is connected with a suitable support arrangement (not shown) for the hand piece, is switched on upon removal of the hand piece from the support arrangement. By means of switch 44 which, in accordance with FIG. 4, is connected with the actuating element 93, there may be provided the option of switching either through pressure or step plate 4 or through actuating member 2, as required. The foot control installation may also be selectively utilized as a mere black-white switch providing for maximum rotational speed (control of the rotational speed may be — if desired — provided from externally of the foot control installation, for example, by a control element in a manually operated grip for the operator), or utilized for the switching including a control function over the actuating member. In the last instance, the rotational speed may be continuously applied. The selective switching is effected from one to the other switching and control modes by imparting pressure to the actuating element 9 through which there is concurrently operated the locking installation for the actuating element 2 as well as the selector switch 44. As can be ascertained from the circuit diagram, upon switching over from the minus pole of the voltage source, the current circuit across switch 40 is opened, and contrastingly the current circuit between the minus pole and the switch 15 is closed. This signifies that, upon displacement of the actuating member 2 from its initial position, the in-out switch 40 remains ineffective, and the motor cannot be actuated through this switch but only by means of the step plate 10. The direction of the rotation of the motor is automatically obtained through the cam control (shown in FIG. 3). If, for example, the actuating member 2 is moved toward the left from its initial position (2″), the switching pin of the switch 41 is actuated, in view of which through contacts 92a the direction of rotation is determined to be towards the left. Correspondingly, this also applies for the clockwise rotational direction of the motor. Both switches 40 and 41 are so positioned relative to the plate cam, and the plate cam is so constructed, that upon movement of the actuating member from its initial position, the switch 41 is actuated prior to the switch 40, whereby at first the direction of rotation of the motor is determined, and only then is the motor actuated. Reference numeral 18 designates the switch, referred to and described with reference to FIG. 2, which is actuated by depressing the actuating elements 19 of the foot contact 3. By means of this switch, spray air is supplied for short periods of time to the hand drill through magnetic valve 87 (so-called chip-blower effect).

An indicator lamp is designated by reference numeral 95, in view of which the selected and effected direction of motor rotation, for example, the principally used rotational direction, is optically indicated.

It is also noted that the foot control installation may be constructed so as to be displaceable from one side only of an initial position. In this type of construction the need for determining the direction of rotation of the motor by means of the foot-controlled actuating element is obviated.

The utilization of the foot control installation is, of course, not limited to dental drill drives and the aforedescribed exemplary embodiments of rotary drill drives or motors. More frequently, the foot control installation may be employed in any type of apparatus in which a predetermined drive condition must be controlled by foot. Consequently, it is conceivable that the control installation may be utilized to provide control over the output or frequency of an oscillator for a tooth filling removal apparatus, or for the control of the operation of an aspirating apparatus. Furthermore, applications in areas other than medical or dental uses are possible, for example, in the control of the rotational speed of electrically driven sewing machines, or the like.

While there has been shown what is considered to be the preferred embodiment of the invention, it will be obvious that modifications may be made which come within the scope of the disclosure of the specification.

What is claimed is:

1. Foot control installation comprising a housing; actuating means supported within said housing for pivotal movement in a horizontal plane and having an end portion extending therefrom, said actuating means being horizontally movable between an initial inoperative position and at least one operative position; foot operator means mounted on the projecting portion of said actuating means for imparting movement to the latter, said foot operator means being imparted a generally linear to slightly concave motion proximate the edge of the housing from which it projects; control and first switching element means operatively connected to said actuating means and adapted to be actuated upon displacement of said actuating means from its initial position; a large-surfaced foot-actuated pressure plate being located at the upper surface of said housing and having downward foot-pressure applied thereto for actuation thereof, said actuating element being positioned in proximity to the path of movement of said foot operator means; and a second switching element being operatively connected to said actuating element so as to be actuated in response to downward foot pressure being imparted thereto.

2. A control installation as claimed in claim 1, the path of movement of said foot contact means being defined by the extent of displacement of said actuating means from its initial to its operative end positions, said pressure plate being of a width extending across the full path of movement of said foot control means from one end position thereof to the other.

3. Control installation as claimed in claim 1, comprising means for supporting said pressure plate in tiltable relationship about an axis extending substantially parallel to the path of movement of said foot contact means.

4. Control installation as claimed in claim 1, said pressure plate being substantially desk-shaped and sloped, and said sloped surface extending toward said foot contact means.

5. Control installation as claimed in claim 4, said sloped surface of said pressure plate extending at an angle of $\alpha = 3°$ to $10°$ with respect to the bottom support surface of said housing.

6. Control installation as claimed in claim 1, comprising an in-and-out switch associated with an electromotor driven drill apparatus, said first switching element adapted to be actuated by said pressure plate being operatively connected to said in-and-out switch.

7. Control installation as claimed in claim 1, comprising a foot support step plate fastened to said housing adjacent the path of movement of said foot operator means of said actuating means, the lower surface of said foot support step plate being coplanar with the lower support surface of said housing.

8. Control installation as claimed in claim 1, comprising a first contact means adapted to be actuated by downward foot pressure being exerted on said foot operator means; and a second contact means being operatively connected to said first contact means.

9. Control installation as claimed in claim 8, said foot operator means comprising a two-piece generally hollow upper and lower cylindrical switch housing for said second contact means, said cylindrical housing portions being axially displaceable relative to each other, the upper portion of said cylindrical housing comprising said first contact means.

10. Control installation as claimed in claim 8, said first switching element being operatively connected to a valve for controlling an inlet conduit of a dental hand member having a supply of air and/or water conveyed thereto through said inlet conduit.

11. Control installation as claimed in claim 1, said housing being substantially rectangularly-shaped, said actuating means in its initial inoperative position extending approximately parallel to the lengthwise sides of said housing.

12. Control installation as claimed in claim 1, comprising a releasable locking arrangement in said housing, said locking arrangement being operatively connected to said actuating means for arresting the latter in at least its operative end position.

13. Control installation as claimed in claim 12, adapted for use with dental drives and electrically-operated drill motors, comprising a selector switch connected with said locking arrangement, said selector switch providing for selective operation by said first switching element responsive to said pressure plate, and alternatively through said actuating means actuating upon its displacement from its initial position a further switching element adapted to effect the in-and-out switching of the drive for said motor.

14. Control installation as claimed in claim 1, said actuating means comprising a pivot arm, said pressure plate being positioned above said pivot arm.

15. Control installation as claimed in claim 1, said control and switching elements forming a connection for use of said installation in conjunction with a dental apparatus.

* * * * *